(12) United States Patent
Cheng et al.

(10) Patent No.: US 7,811,600 B2
(45) Date of Patent: Oct. 12, 2010

(54) NITRIC OXIDE DONATING MEDICAL DEVICES AND METHODS OF MAKING SAME

(75) Inventors: Peiwen Cheng, Santa Rosa, CA (US); Mingfei Chen, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 510 days.

(21) Appl. No.: 11/683,885

(22) Filed: Mar. 8, 2007

(65) Prior Publication Data

US 2008/0220040 A1 Sep. 11, 2008

(51) Int. Cl.
 *A61F 2/00* (2006.01)
 *A61K 31/74* (2006.01)
(52) U.S. Cl. .................. 424/423; 424/78.08; 424/78.12
(58) Field of Classification Search ........................ None
 See application file for complete search history.

(56) References Cited

U.S. PATENT DOCUMENTS

| | | | |
|---|---|---|---|
| 4,954,526 A | 9/1990 | Keefer | |
| 5,155,137 A | 10/1992 | Keefer et al. | |
| 5,212,204 A | 5/1993 | Keefer et al. | |
| 5,250,550 A | 10/1993 | Keefer et al. | |
| 5,268,465 A | 12/1993 | Bredt et al. | |
| 5,339,705 A | 8/1994 | Shirahama et al. | |
| 5,362,718 A | 11/1994 | Skotnicki et al. | |
| 5,366,997 A | 11/1994 | Keefer et al. | |
| 5,380,758 A | 1/1995 | Stamler et al. | |
| 5,405,919 A | 4/1995 | Keefer et al. | |
| 5,428,070 A | 6/1995 | Cooke et al. | |
| 5,468,630 A | 11/1995 | Billiar et al. | |
| 5,525,357 A | 6/1996 | Keefer et al. | |
| 5,574,068 A | 11/1996 | Stamler et al. | |
| 5,583,101 A | 12/1996 | Stamler et al. | |
| 5,650,447 A | 7/1997 | Keefer et al. | |
| 5,658,565 A | 8/1997 | Billiar et al. | |
| 5,665,077 A | 9/1997 | Rosen et al. | |
| 5,718,892 A | 2/1998 | Keefer et al. | |
| 5,891,459 A | 4/1999 | Cooke et al. | |
| 5,900,246 A * | 5/1999 | Lambert ..................... | 424/429 |
| 5,945,452 A | 8/1999 | Cooke et al. | |
| 6,015,815 A | 1/2000 | Mollison | |
| 6,153,588 A * | 11/2000 | Chrzan et al. ................. | 514/18 |
| 6,290,981 B1 | 9/2001 | Keefer et al. | |
| 6,329,386 B1 | 12/2001 | Mollison | |
| 6,403,759 B2 | 6/2002 | Stamler et al. | |
| 6,610,660 B1 | 8/2003 | Saavedra et al. | |
| 6,673,891 B2 | 1/2004 | Stamler et al. | |
| 6,706,274 B2 | 3/2004 | Herrmann et al. | |
| 6,737,447 B1 | 5/2004 | Smith et al. | |
| 6,759,430 B2 | 7/2004 | Anggard et al. | |
| 6,841,166 B1 | 1/2005 | Zhang et al. | |
| 6,875,840 B2 | 4/2005 | Stamler et al. | |
| 6,911,478 B2 | 6/2005 | Hrabie et al. | |
| 6,949,530 B2 | 9/2005 | Hrabie et al. | |
| 6,951,902 B2 | 10/2005 | McDonald et al. | |
| 7,070,798 B1 | 7/2006 | Michal et al. | |
| 7,087,709 B2 | 8/2006 | Stamler et al. | |
| 7,105,502 B2 | 9/2006 | Arnold et al. | |
| 7,378,105 B2 | 5/2008 | Burke et al. | |
| 2002/0094985 A1 | 7/2002 | Herrmann et al. | |
| 2004/0037836 A1 | 2/2004 | Stamler et al. | |
| 2004/0171589 A1 | 9/2004 | Herrmann et al. | |
| 2004/0180131 A1 | 9/2004 | Cheng | |
| 2005/0171596 A1 | 8/2005 | Furst et al. | |
| 2005/0203069 A1 | 9/2005 | Arnold et al. | |
| 2005/0265958 A1 | 12/2005 | West et al. | |
| 2005/0281866 A1 | 12/2005 | Jarrett et al. | |
| 2006/0008529 A1 | 1/2006 | Meyerhoff et al. | |
| 2006/0099235 A1 | 5/2006 | Blakstved et al. | |
| 2006/0121089 A1 | 6/2006 | Michal et al. | |
| 2006/0195142 A1 | 8/2006 | Shalaby | |
| 2006/0251824 A1 | 11/2006 | Boulais et al. | |
| 2007/0014828 A1 | 1/2007 | Fitzhugh et al. | |
| 2007/0053952 A1 | 3/2007 | Chen et al. | |
| 2007/0185561 A1 | 8/2007 | Schmitz et al. | |
| 2007/0264225 A1 | 11/2007 | Cheng et al. | |
| 2008/0220048 A1 | 9/2008 | Chen et al. | |
| 2009/0028966 A1 | 1/2009 | Chen et al. | |
| 2009/0222088 A1 | 9/2009 | Chen et al. | |
| 2009/0232863 A1 | 9/2009 | Cheng et al. | |
| 2009/0232868 A1 | 9/2009 | Chen et al. | |

FOREIGN PATENT DOCUMENTS

| | | |
|---|---|---|
| EP | 0945148 | 9/1999 |
| EP | 0992252 | 4/2000 |

(Continued)

OTHER PUBLICATIONS

Parzuchowski and Meyerhoff, Polymer Preprints, 2001, 42(1), 448-449.*

(Continued)

*Primary Examiner*—Robert A Wax
*Assistant Examiner*—William Craigo

(57) ABSTRACT

Disclosed are implantable medical devices comprising nitric oxide (NO) donating polymers comprising polymer backbones having at least one cyclic amine disposed thereon. Methods are further disclosed for providing nitric oxide-donating polymers.

3 Claims, No Drawings

FOREIGN PATENT DOCUMENTS

| EP | 1300424 | | 4/2003 |
|---|---|---|---|
| WO | WO 95/24908 | * | 9/1995 |
| WO | WO96/15797 | | 5/1996 |
| WO | WO99/01427 | | 1/1999 |
| WO | WO01/10344 | | 2/2001 |
| WO | WO2005/039664 | | 5/2005 |
| WO | WO2005/081752 | | 9/2005 |
| WO | WO2006/037105 | | 4/2006 |
| WO | WO2007/024501 | | 3/2007 |
| WO | WO2007/053292 | | 5/2007 |
| WO | WO2007/053578 | | 5/2007 |

OTHER PUBLICATIONS

Hrabie, Joseph et al., "New Nitric Oxide-Releasing Zwitterions Derived from Polyamines" J. Org. Chem. 1993, 58:1472-1476.

Williams, Jennie et al. "Nitric Oxide-Releasing Nonsteroidal Anti-Inflammatory Drugs (NSAIDs) Alter the Kinetics of Human Colon Cancer Cell Lines More Effectively than Traditional NSAIDs: Implications for Colon Cancer Chemoprevention" Cancer Research, 2001, 61:3285-3289.

Parzuchowski et al., "Synthesis and Characterization of Polymethacrylate-Based Nitric Oxide Donors" J.Am. Chem. Soc., vol. 124, Sep. 20, 2002, pp. 12182-12191.

U.S. Appl. No. 12/340,089, filed Dec. 19, 2008, Chen et al.

U.S. Appl. No. 12/422,425, filed Apr. 13, 2009, Chen et al.

Washington State Univ. Lecture, Chemistry 240, Summer 2001, http://chemistry2.csudh.edu/rpendarvis/aminrxn.html.

Reynolds et al., "Nitric Oxide Releasing Polyurethanes with Covalently Linked Diazeniumdiolated Secondary Amines" Biomacromolecules 2006, 7, 987-994.

Tashiro et al., "Removal of Methyl Orange by Systems of Insoluble Poly(Glycidyl Methacrylate)-G-Tetraethylene-Pentamine and -G-Polyethyleneimines", Research Institute for Polymers and Textiles, 205 (1993) 31-45.

Hrabie et al., "New Nitric Oxide-Releasing Zwitterions Derived from Polyamines" J. Org. Chem, 1993, 58, 1472-1476.

Drago et al., "The Reaction of Notrogen(II) Oxide with Diethylamine" Contribution from the W.A. Noyes Laboratory, University of Illinois, Jun. 24, 1959.

Deng et al., "Polymerization of Lactides and Lactones 11. Ring-Opening Polymerization of x-Acetyl-y-Butyrolactone and Copolymerization with B-Butyrolactone" European Polymer Journal, 36 (2000) 2739-2741.

Lovric et al., "Scope and Limitations of Sodium and Potassium Trimethylsilanolate as Reagents fro Conversion of Esters to Carboxylic Acids" Croatica Chemica Acta, CCACAA 80 (1), 109-115 (2007).

Kireev et al., "Polymerization of Methyl Methacrylate and Vinyl Acetate Initiated by the Manganese Carbonyl-1,2-Epoxy-4,4,4-Trichlorobutance System" Polymer Science, Ser. B, 2006, vol. 48, Nos. 5-6, pp. 138-141.

Frost et al. "Polymers Incorporating Nitric Oxide Releasing/Generating Substances for Improved Biocompatibility of Blood-Contacting Medical Devices" Biomaterials 26 (2005) 1685-1693.

Liu et al., "Diethylenetriamine-Grafted Poly(Glycidyl Methacrylate) Adsorbent for Effective Copper Ion Adsorption" Journal of Colloid and Interface Science 303 (2006) 99-108.

Oh et al., "Spontaneous Catalytic Generation of Nitric Oxide from S-Nitrosothiols at the Surface of Polymer Films Doped with Lipophilic Copper (II) Complex" J. Am. Chem. Soc. 203, 125, pp. 9552-9553, 2003.

Abizaid, Alexandre MD "Novel Approaches to New DES Therapies: Where are we Going?" ACC 2007, New Orleans.

Pasterkamp et al., "Atherosclerotic Plaque Rupture: an Overview" J Clin Basic Cardiol, 2000; 3: pp. 81-96.

Wolfe et al., "Cyclic Hydroxamates, Especially Multiply Substituted [1,2] Oxazinan-3-Ones" Can. J. Chem. 81: 937-960 (2003).

* cited by examiner

NITRIC OXIDE DONATING MEDICAL DEVICES AND METHODS OF MAKING SAME

FIELD OF THE INVENTION

The present invention relates to nitric oxide (NO) donating polymers for fabricating and coating medical devices.

BACKGROUND OF THE INVENTION

Nitric oxide (NO) is a simple diatomic molecule that plays a diverse and complex role in cellular physiology. Less than 25 years ago NO was primarily considered a smog component formed during the combustion of fossil fuels mixed with air. However, as a result of the pioneering work of Ferid Murad et al. it is now known that NO is a powerful signaling compound and cytotoxic/cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOSI, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{2+}$ levels. Increased intracellular $Ca^{2+}$ concentrations results in smooth muscle relaxation which accounts for NO's vasodilating effects. Inducible NOS is responsible for the sustained release of larger amounts of NO and is activated by extracellular factors including endotoxins and cytokines. These higher NO levels play a key role in cellular immunity.

Medical research is rapidly discovering therapeutic applications for NO including the fields of vascular surgery and interventional cardiology. Procedures used to clear blocked arteries such as percutaneous transluminal coronary angioplasty (PTCA) (also known as balloon angioplasty) and atherectomy and/or stent placement can result in vessel wall injury at the site of balloon expansion or stent deployment. In response to this injury a complex multi-factorial process known as restenosis can occur whereby the previously opened vessel lumen narrows and becomes re-occluded. Restenosis is initiated when thrombocytes (platelets) migrating to the injury site release mitogens into the injured endothelium. Thrombocytes begin to aggregate and adhere to the injury site initiating thrombogenesis, or clot formation. As a result, the previously opened lumen begins to narrow as thrombocytes and fibrin collect on the vessel wall. In a more frequently encountered mechanism of restenosis, the mitogens secreted by activated thrombocytes adhering to the vessel wall stimulate overproliferation of vascular smooth muscle cells during the healing process, restricting or occluding the injured vessel lumen. The resulting neointimal hyperplasia is the major cause of a stent restenosis.

Recently, NO has been shown to significantly reduce thrombocyte aggregation and adhesion; this combined with NO's directly cytotoxic/cytostatic properties may significantly reduce vascular smooth muscle cell proliferation and help prevent restenosis. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylactically. This can be accomplished by stimulating endogenous NO production or using exogenous NO sources. Methods to regulate endogenous NO release have primarily focused on activation of synthetic pathways using excess amounts of NO precursors like L-arginine, or increasing expression of nitric oxide synthase (NOS) using gene therapy. U.S. Pat. Nos. 5,945,452, 5,891,459 and 5,428,070 describe sustained NO elevation using orally administrated L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short-lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated. Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. To be effective at preventing restenosis an inhibitory therapeutic such as NO must be administered for a sustained period at therapeutic levels. Consequently, any NO-releasing medical device used to treat restenosis must be suitable for implantation. An ideal candidate device is the vascular stent. Therefore, a stent that safely provides therapeutically effective amounts of NO to a precise location would represent a significant advance in restenosis treatment and prevention.

Nitric oxide-releasing compounds suitable for in vivo applications have been developed by a number of investigators. As early as 1960 it was demonstrated that nitric oxide gas could be reacted with amines, for example, diethylamine, to form NO-releasing anions having the following general formula R—R'N—N(O)NO. Salts of these compounds could spontaneously decompose and release NO in solution. (R. S. Drago et al., J. Am. Chem. Soc. 1960, 82:96-98)

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 and in J. A. Hrabie et al., J. Org. Chem. 1993, 58:1472-1476, all of which are herein incorporated by reference.

The in vivo half-life of NO, however, is limited, causing difficulties in delivering NO to the intended area. Therefore NO-releasing compounds which can produce extended release of NO are needed. Several exemplary NO-releasing compounds have been developed for this purpose, including for example a NO donating aspirin derivative, (*Cancer Research,* 2001, 61:3285-3289), amyl nitrite and isosorbide dinitrate. Additionally, biocompatible polymers having NO adducts (see, for example, U.S. Patent Publications 2006/0008529 and 2004/0037836) and which release NO in a controlled manner have been reported.

Secondary amines have the ability to bind two NO molecules and release them in an aqueous environment. The general structure of exemplary secondary amines capable of binding two NO molecules is depicted in Formula 1, referred to hereinafter a diazeniumdiolate, (wherein M is a counterion, and can be a metal, with the appropriate charge, or a proton and wherein R is a generic notation for organic and inorganic chemical groups). Exposing secondary amines to basic conditions while incorporating NO gas under high pressure leads to the formation of diazeniumdiolates.

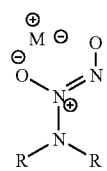

Formula 1

SUMMARY OF THE INVENTION

The present invention provides nitric oxide (NO) donating polymers suitable for fabricating and coating medical devices. More specifically, the present invention provides polymers comprising cyclic amines in the sidechains that can be diazeniumdiolated and release or donate NO in a controlled manner. The polymer sidechains of the present invention are synthesized by coupling reactions.

In one embodiment of the present invention, an implantable medical device is provided comprising a polymer capable of donating nitric oxide wherein the polymer comprises a polymer backbone having at least one cyclic amine disposed thereon.

In another embodiment, the polymer backbone is selected from the group consisting of acrylics, polyethers, polyesters, polyamines, polyurethanes, copolymers thereof, and/or combinations thereof. In another embodiment, the polymer backbone is comprised of at least one monomer selected from the group consisting of polyhydroxy ethylmethacrylate, polyhydroxyl propylmethacrylate, polyvinyl amines, polyvinyl carboxylic acids, polyvinyl alcohol, methyl methacrylate, methacrylic acid, methyl butylmethacrylate, butyl methacrylate, hexyl methacrylate, ethyl acrylate, 2-(ethoxy ethylmethacrylate), methyl acrylate, ethyl acrylate, hexyl acrylate, and butyl acrylate.

In another embodiment of the present invention, the cyclic amine is a piperidine or a piperazine derivative. In yet another embodiment, the piperidine or piperazine derivative is selected from the group consisting of pipecolinic acid, 4-piperieinemethanol, piperazine-2-carboxylic acid, and 4-piperidine butyric acid.

In another embodiment of the present invention, the polymer comprises the general structure of Formula 3;

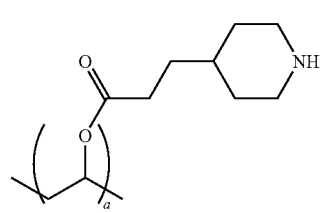

Formula 3 wherein a is an integer from 1 to 20,000.

In another embodiment of the present invention, the polymer comprises the general structure of Formula 4;

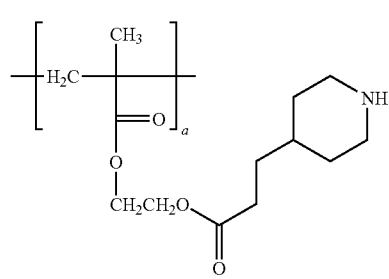

Formula 4 wherein a is an integer from 1 to 20,000.

In another embodiment of the present invention, the polymer comprises the general structure of Formula 5;

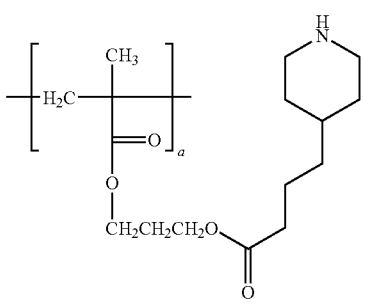

Formula 5 wherein a is an integer from 1 to 20,000.

In another embodiment of the present invention, the polymer comprises the general structure of Formula 6;

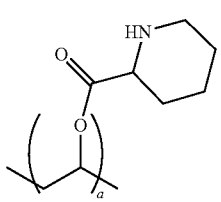

Formula 6 wherein a is an integer from 1 to 20,000.

In another embodiment of the present invention, the polymer comprises the general structure of Formula 7;

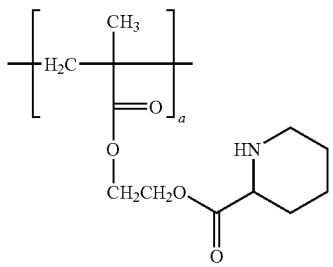

Formula 7 wherein a is an integer from 1 to 20,000.

In another embodiment of the present invention, the polymer comprises the general structure of Formula 8;

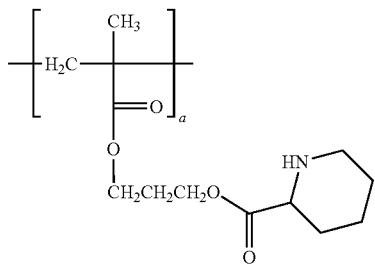

Formula 8 wherein a is an integer from 1 to 20,000.

In another embodiment of the present invention, the polymer comprises the general structure of Formula 10;

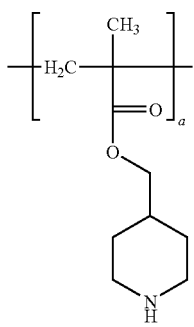

Formula 9 wherein a is an integer from 1 to 20,000.

In another embodiment of the present invention, the medical device is selected from the group consisting of vascular stents, stent grafts, urethral stents, bile duct stents, catheters, guide wires, pacemaker leads, bone screws, sutures and prosthetic heart valves. In yet another embodiment, the implantable medical device is a vascular stent. In another embodiment, the polymer is formed as a coating on a medical device substrate. In another embodiment, the substrate is formed from a material selected from the group consisting of stainless steel, nitinol, aluminum, chromium, titanium, gold, cobalt, ceramics, and polymers. In another embodiment, the medical device is formed from said polymer.

In one embodiment of the present invention, a method of providing a nitric oxide-donating polymer comprises (a) providing a polymer backbone; (b) reacting the polymer backbone with a cyclic amine; and (c) reacting the cyclic amine with nitric oxide under pressure to form a diazeniumdiolate thereof.

In another embodiment, the polymer backbone is selected from the group consisting of acrylics, polyethers, polyesters, polyamines, polyurethanes, copolymers thereof, and/or combinations thereof. In yet another embodiment, the polymer backbone is comprised of at least one monomer selected from the group consisting of polyhydroxy ethylmethacrylate, polyhydroxyl propylmethacrylate, polyvinyl amines, polyvinyl carboxylic acids, polyvinyl alcohol, methyl methacrylate, methacrylic acid, methyl butylmethacrylate, butyl methacrylate, hexyl methacrylate, ethyl acrylate, 2-(ethoxy ethylmethacrylate), methyl acrylate, ethyl acrylate, hexyl acrylate, and butyl acrylate.

In another embodiment of the present invention, the cyclic amine is a piperidine or a piperazine derivative. In another embodiment, the piperidine or piperazine derivative is selected from the group consisting of pipecolinic acid, 4-piperidinemethanol, piperazine-2-carboxylic acid, and 4-piperidine butyric acid.

In one embodiment of the present invention, an implantable medical device is provided wherein the implantable medical device comprises a polymer prepared according to the method of (a) providing a polymer backbone; (b) reacting the polymer backbone with a cyclic amine; and (c) reacting the cyclic amine with nitric oxide under pressure to form a diazeniumdiolate thereof. In another embodiment, the implantable medical device is a vascular stent.

In one embodiment of the present invention, an implantable medical device comprising a polymer coating is provided wherein the polymer is prepared according to the method of (a) providing a polymer backbone; (b) reacting the polymer backbone with a cyclic amine; and (c) reacting the cyclic amine with nitric oxide under pressure to form a diazeniumdiolate thereof. In another embodiment, the implantable medical device is a vascular stent.

DEFINITION OF TERMS

Backbone: As used herein, "backbone" refers to the main chain of a polymer or copolymer of the present invention. A "polyester backbone" as used herein refers to the main chain of a biodegradable polymer comprising ester linkages.

Copolymer: As used herein, a "copolymer" will be defined as a macromolecule produced by the simultaneous chain addition polymerization of two or more dissimilar units such as monomers. Copolymer shall include bipolymers (two dissimilar units), terpolymers (three dissimilar units), etc.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Glass Transition Temperature (Tg): As used herein "glass transition temperature" or Tg refers to a temperature wherein a polymer structurally transitions from a elastic pliable state to a rigid and brittle state.

Mn: As used herein, $M_n$ refers to number-average molecular weight. Mathematically it is represented by the following formula:

$$M_n = \sum_i N_i M_i \bigg/ \sum_i N_i,$$

wherein the $N_i$ is the number of moles whose weight is $M_i$.

$M_w$: As used herein, $M_w$ refers to weight average molecular weight that is the average weight that a given polymer may have. Mathematically it is represented by the following formula:

$$M_w = \sum_i N_i M_i^2 \bigg/ \sum_i N_i M_i,$$

wherein $N_i$ is the number of molecules whose weight is $M_i$.

DETAILED DESCRIPTION OF THE INVENTION

The present invention provides nitric oxide (NO) donating polymers suitable for fabricating and coating medical devices. More specifically, the present invention provides polymers comprising at least one cyclic amine that can be diazeniumdiolated and release or donate NO controllably in a physiological environment. Furthermore, a method for the synthesis of polymers comprising cyclic amine side chains is disclosed.

In one embodiment of the present invention, a method of providing a polymer with reactive cyclic amines is disclosed comprising (a) synthesizing a polymer backbone; (b) bonding cyclic amines to the backbone of the polymer; and (c) reacting the cyclic amine with NO under pressure to form a diazeniumdiolate thereof. The backbones of the polymers of the present invention comprise nucleophilic or electrophilic components that bond to the cyclic amines by means of a corresponding nucleophile or electrophile. Condensation reactions are also employed to bond the cyclic amines to the polymer backbones.

In another embodiment of the method of producing a polymer with reactive cyclic amines, the polymer can comprise, but is not limited to acrylics, polyethers, polyesters, polyamines, polyurethanes, copolymers thereof, and/or combinations thereof. In another embodiment, the polymer is comprised of at least one monomer including, but not limited to, polyhydroxy ethylmethacrylate, polyhydroxyl propylmethacrylate, polyvinyl amines, polyvinyl carboxylic acids, polyvinyl alcohol, methyl methacrylate, methacrylic acid, methyl butylmethacrylate, butyl methacrylate, hexyl methacrylate, ethyl acrylate, 2-(ethoxy ethylmethacrylate), methyl acrylate, ethyl acrylate, hexyl acrylate, and butyl acrylate.

In another embodiment, the cyclic amines include, but are not limited to, ring sizes ranging from 2 to 12 carbons. In one embodiment the cyclic amine is a piperidine, or a derivative thereof. The piperidine moiety has the general structure of Formula 2 and further comprises a function group R. To bond the piperidine moiety to the polymer backbone, a variety of independent functional groups in different ring positions (depicted as R in Formula 2) are employed as depicted in Formula 2.

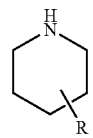

Formula 2

In Formula 2, R comprises a C1 to C10 hydrocarbon that has a group reactive towards an electrophile and optionally a nucleophile. In one embodiment the piperidine derivative includes but is not limited to pipecolinic acid, 4-piperdinemethanol, piperazine-2-carboxylic acid, and 4-piperidine butyric acid.

In one embodiment of the present invention, the polymers have side chains comprising cyclic amines such as, but not limited to, piperidine derivatives. In embodiments of the methods of the present invention, the piperidine derivatives are introduced through condensation reactions of the independent functional groups with the backbone of the polymer.

In one embodiment, the polymer is polyvinyl alcohol which is reacted with the piperidine 4-piperidine butyric acid (Reaction 1) to produce a polymer having the general structure of Formula 3. The polymer of Formula 3 is suitable for diazoniumdiolation.

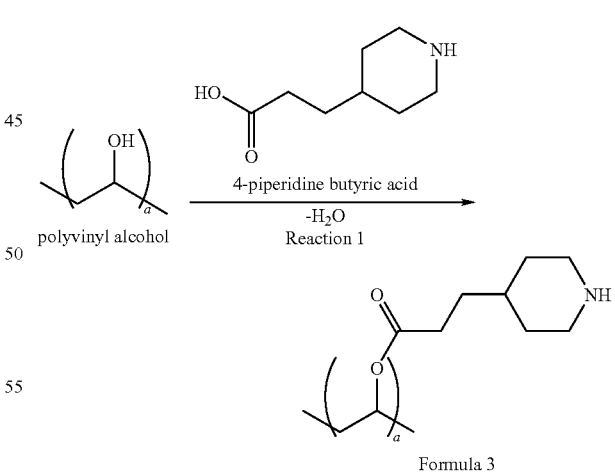

Formula 3

In one embodiment of Formula 3, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000;

from 1,500 to 6,000; from 1,600 to 5,000; from 1,600 to 4,000; from 1,700 to 3,000; from 1,800 to 2,000; or from 1,900 to 1,950.

In another embodiment, the polymer is polyhydroxyl ethyl methacrylate which is reacted with the piperidine 4-piperidine butyric acid (Reaction 2) to produce a polymer having the general structure of Formula 4. The polymer of Formula 4 is suitable for diazoniumdiolation.

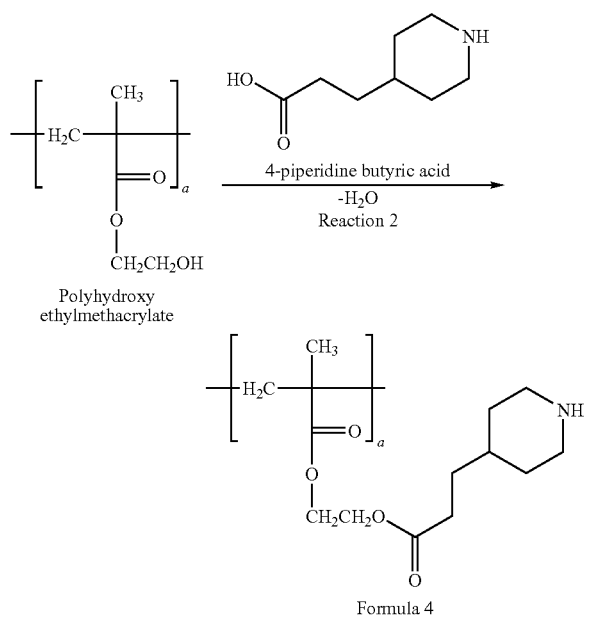

Formula 4

In one embodiment of Formula 4, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000; from 1,500 to 6,000; from 1,600 to 5,000; from 1,600 to 4,000; from 1,700 to 3,000; from 1,800 to 2,000; or from 1,900 to 1,950.

In yet another embodiment, the polymer is polyhydroxyl propyl methacrylate which is reacted with the piperidine 4-piperidine butyric acid (Reaction 3) to produce a polymer having the general structure of Formula 5. The polymer of Formula 5 is suitable for diazoniumdiolation.

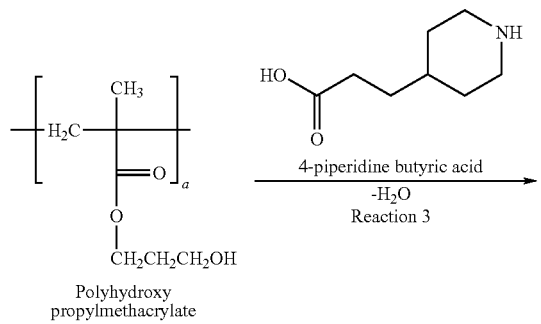

-continued

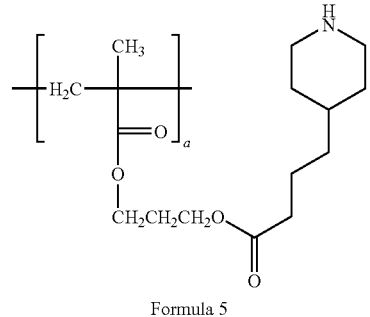

Formula 5

In one embodiment of Formula 5, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000; from 1,500 to 6,000; from 1,600 to 5,000; from 1,600 to 4,000; from 1,700 to 3,000; from 1,800 to 2,000; or from 1,900 to 1,950.

In another embodiment, the polymer is polyvinyl alcohol which is reacted with the piperidine pipecolinic acid (Reaction 4) to produce a polymer having the general structure of Formula 6. The polymer of Formula 6 is suitable for diazoniumdiolation.

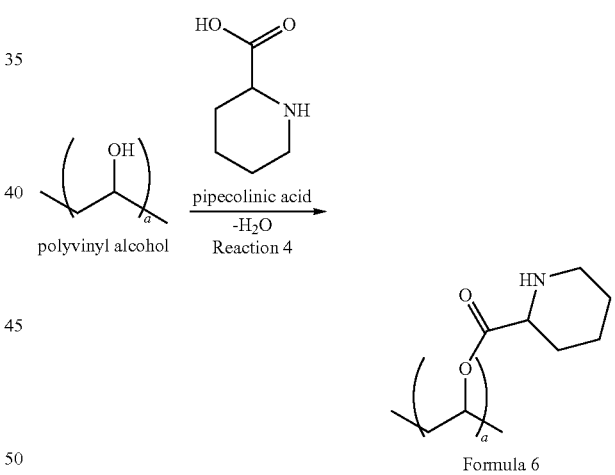

Formula 6

In one embodiment of Formula 6, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000; from 1,500 to 6,000; from 1,600 to 5,000; from 1,600 to 4,000; from 1,700 to 3,000; from 1,800 to 2,000; or from 1,900 to 1,950.

In another embodiment, the polymer is polyhydroxy ethylmethacrylate which is reacted with the piperidine pipecolinic acid (Reaction 5) to produce a polymer having the general structure of Formula 7. The polymer of Formula 7 is suitable for diazoniumdiolation.

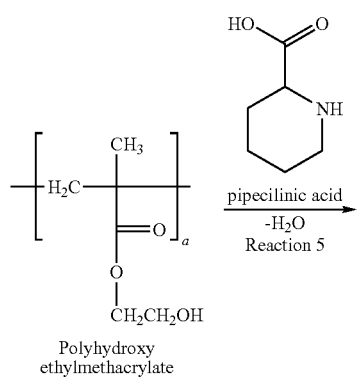

Polyhydroxy
ethylmethacrylate

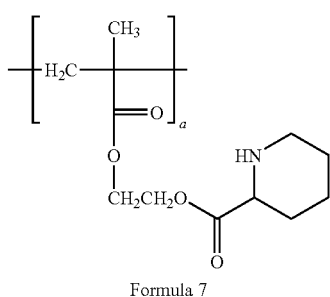

Formula 7

In one embodiment of Formula 7, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000; from 1,500 to 6,000; from 1,600 to 5,000; from 1,600 to 4,000; from 1,700 to 3,000; from 1,800 to 2,000; or from 1,900 to 1,950.

In another embodiment, the polymer is polyhydroxy propylmethacrylate which is reacted with the piperidine pipecolinic acid (Reaction 6) to produce a polymer having the general structure of Formula 8. The polymer of Formula 8 is suitable for diazoniumdiolation.

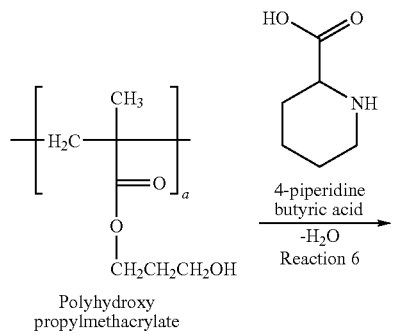

Polyhydroxy
propylmethacrylate

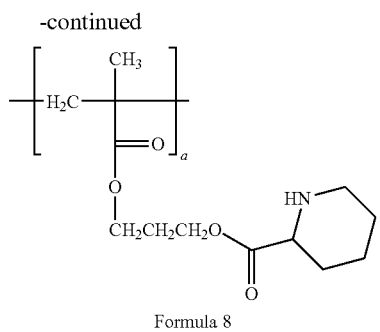

Formula 8

In one embodiment of Formula 8, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000; from 1,500 to 6,000; from 1,600 to 5,000; from 1,600 to 4,000; from 1,700 to 3,000; from 1,800 to 2,000; or from 1,900 to 1,950.

In another embodiment, the polymer is polymethacrylic acid which is reacted with the piperidine Boc-4-piperidinemethanol (Reaction 7) to produce a polymer having the general structure of Formula 9. Then the Boc (tert-butyl carbamate) group of Formula 9 is removed yielding a polymer having the general structure of Formula 10. The polymer of Formula 10 is suitable for diazoniumdiolation.

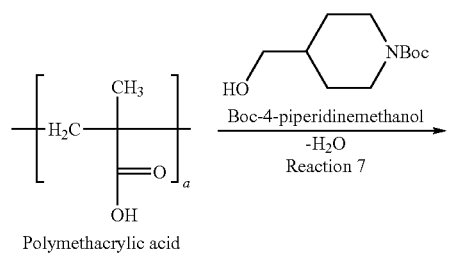

Polymethacrylic acid

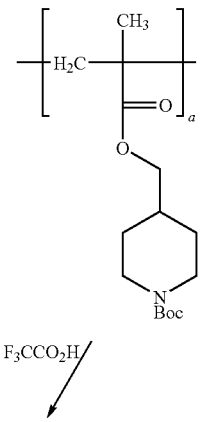

-continued

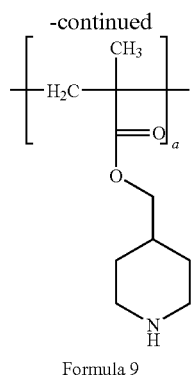

Formula 9

In one embodiment of Formula 8, a is an integer ranging from 1 to 20,000. In additional embodiments, a ranges from 10 to 19,000; from 100 to 18,000; from 200 to 17,000; from 300 to 16,000; from 400 to 15,000; from 500 to 14,000; from 600 to 13,000; from 700 to 12,000; from 800 to 11,000; from 900 to 12,000; from 1,000 to 11,000; from 1,100 to 10,000; from 1,200 to 9,000; from 1,300 to 8,000; from 1,400 to 7,000; from 1,500 to 6,000; from 1,600 to 5,000; from 1,600 to 4,000; from 1,700 to 3,000; from 1,800 to 2,000; or from 1,900 to 1,950.

Physical properties of the polymers in the present invention can be fine tuned so that the polymers can optimally perform for their intended use. Properties that can be fine tuned, without limitation, include Tg, molecular weight (both $M_n$ and $M_w$), polydispersity index (PDI, the quotient of $M_w/M_n$), degree of elasticity and degree of amphiphlicity. In one embodiment of the present invention, the Tg of the polymers range from about –10° C. to about 85° C. In still another embodiment of the present invention, the PDI of the polymers range from about 1.35 to about 4. In another embodiment of the present invention, the Tg of the polymers ranges form about 0° C. to about 40° C. In still another embodiment of the present invention, the PDI of the polymers range from about 1.5 to about 2.5.

Implantable medical devices suitable for coating with the NO-donating polymers of the present invention include, but are not limited to, vascular stents, stent grafts, urethral stents, bile duct stents, catheters, guide wires, pacemaker leads, bone screws, sutures and prosthetic heart valves. The polymers of the present invention are also suitable for fabricating implantable medical devices. Medical devices which can be fabricated from the NO-donating polymers of the present invention include, but are not limited to, vascular stents, stent grafts, urethral stents, bile duct stents, catheters, guide wires, pacemaker leads, bone screws, sutures and prosthetic heart valves.

The polymer coatings of the present invention are intended for medical devices deployed in a hemodynamic environment and possess excellent adhesive properties. That is, the coating must be stably linked to the medical device surface. Many different materials can be used to fabricate the substrate of the implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the polymeric coatings made in accordance with the teachings of the present invention. Furthermore, the polymers of the present invention can be used to fabricate an entire medical device.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The NO donating polymeric coatings of the present invention can be applied to medical device surfaces, either primed or bare, in any manner known to those of ordinary skill in the art. Application methods compatible with the present invention include, but are not limited to, spraying, dipping, brushing, vacuum-deposition, and others. Moreover, the NO donating polymeric coatings of the present invention may be used with a cap coat. A cap coat as used herein refers to the outermost coating layer applied over another coating. A NO donating polymer coating of the present invention is applied over the primer coat. Then, a polymer cap coat is applied over the NO donating polymeric coating of the present invention. The cap coat may optionally serve as a diffusion barrier to control the NO release. The cap coat may be merely a biocompatible polymer applied to the surface of the sent to protect the stent and have no effect on the NO release rates.

The NO donating polymers of the present invention are also useful for the delivery and controlled release of drugs. Drugs that are suitable for release from the polymers of the present invention include, but are not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In one embodiment of the present invention the drugs controllably released include, but are not limited to, macrolide antibiotics including FKBP-12 binding agents. Exemplary drugs of this class include sirolimus (rapamycin) (Formula 2), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent application Ser. No. 10/930,487) and zolimus (ABT-578; see U.S. Pat. Nos. 6,015,815 and 6,329, 386) (Formula 1). Additionally, and other rapamycin hydroxyesters as disclosed in U.S. Pat. No. 5,362,718 may be used in combination with the polymers of the present invention. The entire contents of all of preceding patents and patent applications are herein incorporated by reference for all they teach related to FKBP-12 binding compounds and the derivatives.

EXAMPLES

The following non limiting examples provide methods for the synthesis of exemplary polymers according to the teachings of the present invention.

Example 1

Example 1 is illustrative of a non-limiting synthetic method to produce a cyclic-amine containing polymer according to the teachings of the present invention.

To a 500 mL three-neck round bottom glass equipped with a mechanical stirrer is added polyhydroxy propylmethacrylate (7.7 g, 0.54 mmol) in a mixture of n-propyl alcohol and 2-butanone (70:30, 2-butanone:n-propyl alcohol, 300 mL) and 2,2'-azobis(2-methylpropionitrile) (1.36 g, 0.8 wt. %). A net positive pressure of nitrogen is introduced and the reaction heated (60° C.) for 5 hours. The reaction is then allowed to cool (23° C.). The polymer solution is poured into cold methanol (−60° C.) and a white polymer is precipitated out. All the solvents are decanted and the polymer is re-dissolved in chloroform. This procedure is repeated three times. Then, the polymer is placed in vacuum and the solvent removed in vacuo, yielding the solid polymer.

Example 2

Example 2 is illustrative of a non-limiting esterification reaction between a polymer of the present invention and a cyclic amine having the general structure of Formula 2.

To a reaction vessel containing the polymer and the cyclic amine having the general structure of Formula 2 is added a dehydration agent such as, but not limited to molecular sieves and a catalyst such as, but not limited to sulfuric acid. The reaction is stirred and once complete the solvent is removed in vacuo. The polymers are washed with water and a suitable organic solvent then dried.

Example 3

Example 3 is illustrative of the non-limiting example of the formation of diazeniumdiolates, i.e. incorporation of nitric oxide (NO) in the polymer.

Polymers dissolved (typically 10 mg/50 mL) in 2,4,7-trinitro-9-fluorenone (THF) are placed in a high pressure reaction vessel. An inert gas (including, but not limited to, argon and nitrogen) is then purged through the vessel. A base dissolved in a solvent (typically sodium methoxide or potassium methoxide in methanol) is then added in excess (typically 110% to 200%). The reaction is allowed to stir and the vessel purged with NO gas. The pressure of NO gas is increased (typically at least 15 psi) and the reaction mixture is then stirred further for at least 24 hours. At the end of the required time for the formation of diazeniumdiolates, dry hydrophobic solvents (typically hexanes or methyl tert-butyl ether) are added to aid in the precipitation of the polymers. The polymers are then filtered and dried.

Example 4

Example 4 is illustrative of the formation of diazeniumdiolates on vascular stents coated with the cyclic amine-containing polymers of the present invention.

A vascular stent coated with at least one polymer from Examples 2 and 3 is placed in a 13 mm×100 mm glass test tube. Ten milliliters of 3% sodium methoxide in methanol or acetonitrile is added to the test tube, which is then placed in a 250 mL stainless steel Parr® apparatus. The apparatus is degassed by repeated cycles (×10) of pressurization/depressurization with nitrogen gas at 10 atmospheres. Next, the vessel undergoes 2 cycles of pressurization/depressurization with NO at 30 atmospheres. Finally, the vessel is filled with NO at 30 atmospheres and left at room temperature for 24 hrs. After 24 hrs, the vessel is purged of NO and pressurized/depressurized with repeated cycles (×10) of nitrogen gas at 10 atmospheres. The test tube is removed from the vessel and the 3% sodium methoxide solution is decanted. The stent is then washed with 10 mL of methanol (×1) and 10 mL of diethyl ether (×3). The stent is then removed from the test tube and dried under a stream of nitrogen gas. This procedure results in a diazeniumdiolated polymer-coated vascular stent.

Example 5

The present invention pertains to cyclic amine-containing polymers used for the manufacture of medical devices and medical devices coatings. Example 5 discloses a non-limiting method for manufacturing stents made of cyclic amine-containing polymers according to the teachings of the present invention.

For exemplary, non-limiting, purposes a vascular stent will be described. A cyclic amine-containing polymer made according to the teachings of the present invention is heated until molten in the barrel of an injection molding machine and forced into a stent mold under pressure. After the molded polymer (which now resembles and is a stent) is cooled and solidified the stent is removed from the mold. In one embodiment of the present invention the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube. In the braided stent embodiment monofilaments are fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a temperature between about the polymer glass transition temperature and the melting temperature of the polymer blend for a time period between about five minutes and about 18 hours in air, an inert atmosphere or under vacuum. The stent is then allowed to cool and is then cut.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable medical device comprising a polymer capable of donating nitric oxide wherein said polymer comprises the general structure of Formula 5;

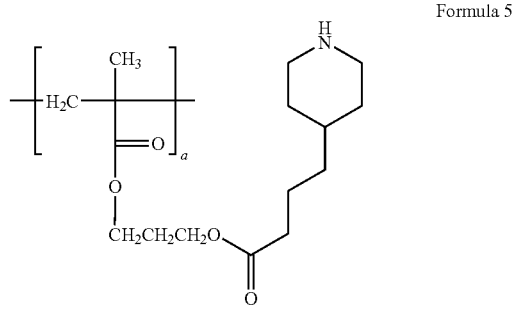

Formula 5 wherein a is an integer from 1 to 20,000.

2. A method of providing the nitric oxide-donating polymer of claim 1 comprising:
   (a) providing the polymer backbone;
   (b) reacting said polymer backbone with the cyclic amine; and
   (c) reacting said cyclic amine with nitric oxide under pressure to form a diazeniumdiolate thereof.

3. The method according to claim 2 wherein said polymer backbone is further comprised of at least one monomer selected from the group consisting of polyhydroxy ethylmethacrylate, polyhydroxyl propylmethacrylate, polyvinyl amines, polyvinyl carboxylic acids, polyvinyl alcohol, methyl methacrylate, methacrylic acid, methyl butyl methacrylate, butyl methacrylate, hexyl methacrylate, ethyl acrylate, 2-(ethoxyethylmethacrylate), methyl acrylate, ethyl acrylate, hexyl acrylate, and butyl acrylate.

\* \* \* \* \*